(12) United States Patent
Kuntz et al.

(10) Patent No.: US 10,047,013 B2
(45) Date of Patent: *Aug. 14, 2018

(54) ZIRCONIA-BASED MONOPHASE AND MULTIPHASE MATERIALS

(71) Applicant: CeramTec GmbH, Plochingen (DE)

(72) Inventors: Meinhard Kuntz, Esslingen (DE); Kilian Friederich, Plochingen (DE); Lukas Gottwik, Heiningen (DE); Andreas Morhardt, Esslingen (DE); Juliane Ehrlich, Stuttgart (DE)

(73) Assignee: CeramTec GmbH, Plochingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/766,184

(22) PCT Filed: Feb. 7, 2014

(86) PCT No.: PCT/EP2014/052407
§ 371 (c)(1),
(2) Date: Aug. 6, 2015

(87) PCT Pub. No.: WO2014/124874
PCT Pub. Date: Aug. 21, 2014

(65) Prior Publication Data
US 2015/0376067 A1 Dec. 31, 2015

(30) Foreign Application Priority Data

Feb. 13, 2013 (DE) .......................... 10 2013 202 287

(51) Int. Cl.
C04B 35/48 (2006.01)
A61C 5/77 (2017.01)
(Continued)

(52) U.S. Cl.
CPC ................ *C04B 35/48* (2013.01); *A61C 5/70* (2017.02); *A61C 5/77* (2017.02); *A61C 8/005* (2013.01);
(Continued)

(58) Field of Classification Search
CPC ...... C04B 35/486; C04B 35/488; C04B 35/49
See application file for complete search history.

(56) References Cited

U.S. PATENT DOCUMENTS 4,316,964 A 2/1982 Lange
4,690,910 A * 9/1987 Tsukuma ............. C04B 35/486
501/103

(Continued)

FOREIGN PATENT DOCUMENTS

DE 40 20 893 A1 1/1991
DE 195 40 452 A1 3/1997
(Continued)

OTHER PUBLICATIONS

Miura, et al. "Formation of plate-like lanthanum-β-Aluminate crystal in Ce-TZP matrix", J. of Material Science 29 (1994), pp. 262-268.

(Continued)

Primary Examiner — Karl E Group
(74) Attorney, Agent, or Firm — Norton Rose Fulbright US LLP

(57) ABSTRACT

Zirconium oxide material and a sintered molded body produced from the material. The zirconium oxide is present in the tetragonal phase in an amount of 70 to 99.9 vol.-%. The tetragonal phase is chemically stabilized with rare-earth oxides. The sintered moldings can be used, e.g., in the medical field as implants or as dental prostheses.

19 Claims, 7 Drawing Sheets

Figure 1:
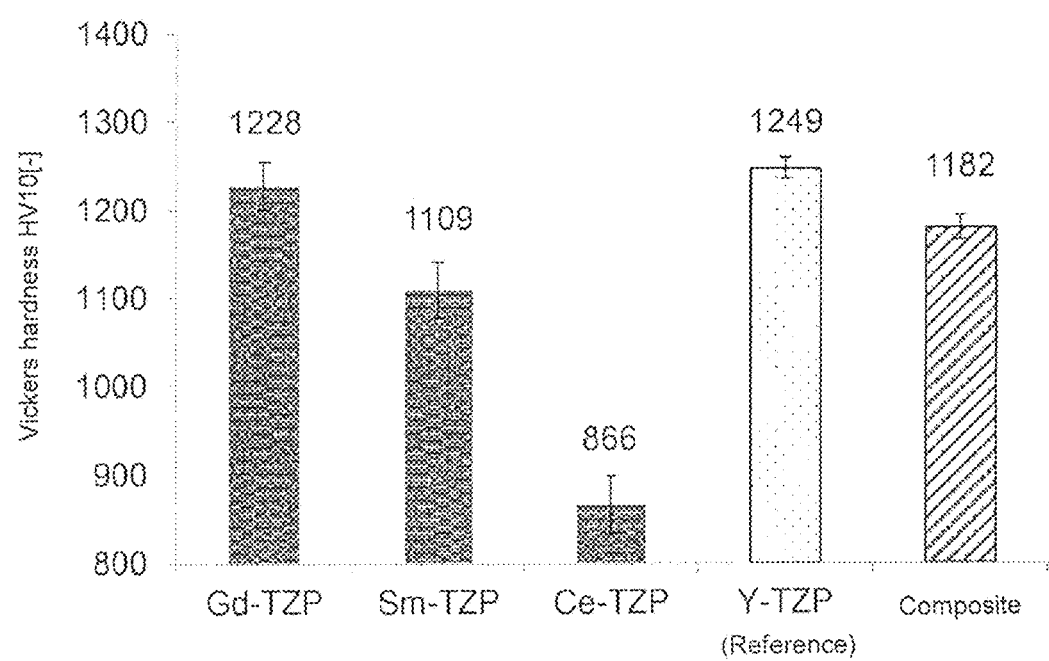

(51) Int. Cl.

| | | |
|---|---|---|
| A61C 13/083 | (2006.01) | |
| C04B 35/486 | (2006.01) | |
| C04B 35/488 | (2006.01) | |
| A61L 27/02 | (2006.01) | |
| A61C 8/00 | (2006.01) | |
| A61K 6/00 | (2006.01) | |
| A61K 6/02 | (2006.01) | |
| A61C 13/08 | (2006.01) | |
| A61C 5/70 | (2017.01) | |
| A61C 13/00 | (2006.01) | |

(52) U.S. Cl.
CPC .......... *A61C 8/0012* (2013.01); *A61C 13/082* (2013.01); *A61C 13/083* (2013.01); *A61K 6/0044* (2013.01); *A61K 6/023* (2013.01); *A61K 6/024* (2013.01); *A61K 6/025* (2013.01); *A61K 6/0225* (2013.01); *A61K 6/0255* (2013.01); *A61L 27/025* (2013.01); *C04B 35/486* (2013.01); *C04B 35/488* (2013.01); *A61C 13/0022* (2013.01); *A61L 2430/38* (2013.01); *C04B 2235/3213* (2013.01); *C04B 2235/3222* (2013.01); *C04B 2235/3224* (2013.01); *C04B 2235/3227* (2013.01); *C04B 2235/3229* (2013.01); *C04B 2235/612* (2013.01); *C04B 2235/765* (2013.01); *C04B 2235/785* (2013.01); *C04B 2235/96* (2013.01)

(56) References Cited

U.S. PATENT DOCUMENTS

| 4,820,666 | A | * | 4/1989 | Hirano .................. C04B 35/119 |
| | | | | 501/104 |
| 5,002,911 | A | | 3/1991 | Matsumoto et al. |
| 5,017,532 | A | * | 5/1991 | Sonnenberg .......... C04B 35/486 |
| | | | | 501/103 |
| 5,232,878 | A | | 8/1993 | Kasuga et al. |
| 5,525,560 | A | | 6/1996 | Yamazaki et al. |
| 5,863,850 | A | | 1/1999 | Nawa et al. |
| 7,012,036 | B2 | * | 3/2006 | Nawa .................. C04B 35/4885 |
| | | | | 501/105 |
| 7,056,851 | B2 | | 6/2006 | Nawa |
| 7,148,167 | B2 | | 12/2006 | Shikata et al. |
| 7,291,574 | B2 | * | 11/2007 | Tanaka .................. C01G 25/02 |
| | | | | 501/103 |
| 7,928,028 | B2 | | 4/2011 | Nawa et al. |
| 8,093,168 | B2 | | 1/2012 | Nawa et al. |
| 8,614,001 | B2 | | 12/2013 | Nonnet et al. |
| 8,889,576 | B2 | | 11/2014 | Höland et al. |
| 2007/0049484 | A1 | | 3/2007 | Kear et al. |
| 2009/0292366 | A1 | * | 11/2009 | Burger ................ C04B 35/4885 |
| | | | | 623/23.56 |
| 2009/0317767 | A1 | * | 12/2009 | Burger ................ C04B 35/4885 |
| | | | | 433/201.1 |
| 2011/0254181 | A1 | * | 10/2011 | Holand ................ A61K 6/0008 |
| | | | | 264/6 |
| 2011/0262770 | A1 | * | 10/2011 | Torigoe ................ C04B 35/486 |
| | | | | 428/633 |
| 2012/0252656 | A1 | | 10/2012 | Kuntz et al. |
| 2012/0295113 | A1 | | 11/2012 | Kurizoe et al. |
| 2015/0035210 | A1 | | 2/2015 | Holand et al. |
| 2015/0175485 | A1 | * | 6/2015 | Gottwik ................ A61L 27/10 |
| | | | | 514/770 |

FOREIGN PATENT DOCUMENTS

| DE | 10 2008 042 015 A1 | | 3/2010 |
| EA | 011425 B1 | | 2/2009 |
| EP | 2 377 506 A1 | | 10/2011 |
| JP | 61201661 | * | 9/1986 |
| JP | 08033650 | * | 2/1996 |
| WO | 90/11980 A1 | | 10/1990 |
| WO | 2008/040813 A1 | | 4/2008 |
| WO | 2011/083023 A1 | | 7/2011 |
| WO | 2013/004361 A2 | | 1/2013 |
| WO | 2014/029757 A1 | | 2/2014 |

OTHER PUBLICATIONS

Shen, et al. "Dense Hydroxyapatite-Zirconia Ceramic Composites with High Strength for Biological Applications", Advanced Materials, 13 No. 3, (2001), pp. 214-216.

Saidi, et al. "Fluorinated Comblike Homopolymers: The Effect of Spacer Length on Surface Properties", J. of Polymer Science: Part A: Polymer Chemistry, vol. 43 (2005), pp. 3737-3747.

* cited by examiner

ZIRCONIA-BASED MONOPHASE AND MULTIPHASE MATERIALS

This application is a § 371 of International Application No. PCT/EP2014/052407 filed Feb. 7, 2014, and claims priority from German Patent Application No. 10 2013 202 287.5 filed Feb. 13, 2013.

The invention relates to the production and use of single-phase and multiphase materials based on zirconia. In particular the invention relates to single-phase polycrystalline materials based on zirconia as well as sintered moldings produced from this material, which can be used in the medical field as implants or as dental prostheses, for example.

The zirconia ceramic is biocompatible and can be produced using traditional and standardized processing methods. The mechanical properties and the hydrothermal aging resistance are adapted with regard to a damage-free hard processability and the field of use and/or milieu. The higher level field of application of zirconia ceramics is in the field of bioceramics. Lower level application fields include, for example, dental prostheses (blanks, bridges and crowns), dental implants, abutments and spinal implants (cages, spacers) as well as general application fields, which require an engineering ceramic with damage-free hard processability, e.g., in machining processes such as grinding, milling and drilling.

Ceramic materials have advantages in the dental market in comparison with traditional metallic materials because of their chemical stability, their mechanical, physical and in particular optical properties, which allow excellent aesthetic results.

The general trend with dental ceramics is in the direction of "all-ceramic systems." Nevertheless, ceramics today are often applied as veneers to metallic structures.

Dental ceramics can be classified on the basis of their production method and their crystalline phase. A fundamental distinction is made between metal-ceramic systems and all-ceramic systems.

Metal-ceramic systems have been in existence since 1960. To obtain an aesthetically acceptable restoration based on the natural tooth, a veneer ceramic is applied to a metal framework. Typical veneer materials consist of feldspar-like glasses, usually based on leucite crystals. Adding leucite crystals ($KAlSi_2O_6$) to the feldspar-like glass structure leads to optimal properties with regard to the thermal expansion coefficients of the framework and the veneer. Leucite crystals are formed due to incongruent melting of natural feldspar at temperatures between 1150 and 1530° C. The thermal expansion coefficient can be controlled in a targeted manner by varying the leucite crystal content in the glass and can be adapted to the metal framework. The typical leucite crystal content in feldspar-type glass usually amounts to between 15 and 25 vol %. The thermal expansion coefficient is therefore lower than that of the metal, so that the applied veneer is put under pressure after cooling.

Traditionally, veneer ceramics are sintered in vacuo to reduce the porosity in the end product. The mechanical properties, in particular the strength and fracture toughness of the leucite crystal-based glasses (also known as dental porcelain), are the lowest of all ceramic materials used in dentistry because of the glass phase. By 2005, 50% of all dental restorations were still being produced using metal-ceramic systems.

All-ceramic systems are free of metal and have been available for 30 years. The process technology is constantly being developed further (e.g., hot pressing, slip casting, CAD/CAM processing). The main difference from the metallic ceramic systems is a much higher crystalline phase content between 35 and 100 vol %. The mechanical properties are improved, but the opacity is also increased, which is a disadvantage with regard to the required aesthetics. There are a number of factors having an influence on the durability of all-ceramic systems, e.g., the oral medium, fluctuating pH levels from acidic to basic, cyclic loading or extreme load peaks during chewing. All-ceramic systems with a higher glass phase content often exhibit stress corrosion cracking as a cause of failure. Because of hydrothermal aging of Y-TZP ceramics (yttria-stabilized tetragonal zirconia polycrystal with 100 vol % crystalline phase) at low temperatures, tests based on standards are required, in which the durability in a human environment and with cyclic loading is to be evaluated.

All-ceramic systems are classified mainly on the basis of the production method (e.g., hot pressing, dry pressing and sintering, slip casting, CAD/CAM machining).

In hot pressing, leucite crystal-based glasses with a crystalline phase content between 35 and 45 vol % have been used first. The strength of the leucite crystal-based glasses is approximately 150 MPa, which is thus higher by a factor of about 2 than is the case with leucite crystal-based glasses of the metal-ceramic systems. Repeated heating can facilitate leucite crystallization and yield higher strength results.

A new glass ceramic is used for hot pressing today. This material consists of a lithium disilicate-based glass with a crystalline phase content of 65 vol %. Radiographic studies have revealed additional crystal phases such as lithium metasilicate ($Li_2SiO_3$) and cristobalite ($SiO_2$) in addition to lithium disilicate ($Li_2Si_2O_5$). The strength is higher by a factor of approximately 2 in comparison with the leucite crystal-based glasses and is approximately 250 MPa.

Dry pressing and sintering of all-ceramic systems have been used since the early 1900s. They are produced in computer-assisted processes which take into account the sintering shrinkage of the pressed object in sintering. Alumina and zirconia-based ceramics are used as the structural material (100 vol % crystalline phase content), wherein a veneer of glass ceramic is additionally applied to the structural material. Alumina ceramics are characterized by a bending strength of approximately 600 MPa and an excellent in vivo behavior.

Slip casting has been used since the 1990s. In this process a porous green body is produced by means of slip casting from crystalline phase, then sintered and infiltrated with a glass based on lanthanum. The following glass ceramics are available on the dental market: alumina ($Al_2O$), spinel ($MgAl_2O_4$) or 12Ce-TZP/$Al_2O_3$ composite. Glass-infiltrated alumina has mechanical properties comparable to those of lithium disilicate-based glass ceramic but a minimally higher opacity. Glass-infiltrated spinel has a much greater translucency and mechanical properties comparable to those of glass ceramic based on lithium disilicate. Glass-infiltrated zirconia/alumina composite has the highest strength and fracture toughness of all slip-cast dental ceramics.

Computer-controlled CAD/CAM processing of ceramic blocks and/or blanks was introduced by Duret and has been practiced since the early 1970s. At that time, densely sintered blanks were used for processing. Today, work is done mainly using presintered blanks.

Glass ceramic is suitable for CAD/CAM processing in a densely sintered state based on the very good processability. In the past typical mica crystal-based glasses were used because of their ideal processability. Today feldspar glasses containing sanidine, leucite or lithium disilicate crystals.

However, CAD/CAM processing on densely sintered glass ceramics shows significant tool wear. Surface defects can have a negative influence on the in vivo behavior.

Glass ceramics can generally be processed well. However, microcracks develop along the phase boundaries during cooling due to the different thermal expansion coefficients of the crystal and the glass matrix. In addition, the crystalline phases have a very good cleavability along the longitudinal direction (mainly mica along the crystallographic (001) plane). The crystal phases should therefore not have any preferential orientation in the glass structure. A crack introduced by a tool will run along cleavage planes or also along phase boundaries between the crystal and the glass matrix. Therefore, the crack is constantly being deflected during processing and only small regions of the surface are chipped out of the workpiece. This strengthening mechanism is also known by the term "crack deflection."

Since 2001, CAD/CAM processing has been performed on presintered zirconia blanks. Processing is easier and faster and causes less tool wear in comparison with hard processing on densely sintered zirconia blanks. However, the finished workpieces must be densely sintered subsequently. Fluctuations in sintering shrinkage associated with dimensional deviations as well as follow-up correctional work by hand by the dental technician result in an increased risk of damage to the zirconia. Almost all the available zirconia blanks are made from Tosoh raw material. Zirconia as the framework material has the best mechanical properties so far, but cracks due to the phase transition of the tetragonal zirconia phase often occur at the interface between the framework and the veneer due to the veneer ceramic that is additionally required. Many 3-year and 5-year in vivo studies have already been published for several years now. The conclusion of these studies is that the success rate is excellent but the survival rate is low when there are complications such as caries or chipping of the veneer. The current development trend is definitely in the direction of zirconia/alumina veneer materials with the goals of improving hydrothermal aging resistance and mechanical properties.

The object of the invention is therefore to provide an improved ceramic material based on zirconia, in particular for the field of dental ceramics that will combine good mechanical properties with a lower hardness as well as improved damage tolerance and can be processed by means of conventional methods.

This object is achieved by a material and sintered molding according to the independent claims.

Accordingly, a zirconia material according to the invention comprises, zirconia, 70 to 100 vol % of which is present in the tetragonal phase, wherein the tetragonal phase of the zirconia is chemically stabilized using oxides of the rare earths as chemical stabilizers.

Within the scope of this invention, the term "material" is understood to refer to a finished sintered ceramic. The compositions that are described thus relate to a sintered ceramic body, unless otherwise indicated.

The invention relates to single-phase or multiphase ceramic materials based on tetragonal zirconia. The tetragonal phase of zirconia is stabilized by using oxides of the rare earths as additives. Preferred oxides of the rare earths include cerium oxide ($CeO_2$), especially preferably samarium oxide ($Sm_2O_3$) and gadolinium oxide ($Gd_2O_3$). The zirconia phase is the main component and is fundamentally represented in the material with a volume amount of 70-100%.

A zirconia material according to the invention especially preferably contains between 94 and 99.9 vol % $ZrO_2$ and between 0.1 and 6 vol % of a thermodynamically stable aluminate. Such a material is referred to as a "composite material" within the scope of this invention.

In an especially preferred embodiment of the invention, the amount of zirconia by volume is approximately 95 vol % of the total volume of material. A second main component consists of a thermodynamically stable aluminate, preferably strontium aluminate or lanthanum aluminate with an amount by volume of approximately 5 vol %. The second main component especially preferably consists of more than 80 vol % strontium aluminate or lanthanum aluminate.

In another especially preferred variant of the zirconia material, the amount by volume of the zirconia is between 98 and 99.9%, i.e., in the technical sense it is predominantly a monophase material.

It has surprisingly been found that the recipes for materials according to the invention are especially suitable for a low-damage hard processing, i.e., the material properties are hardly impaired at all even under unfavorable processing conditions.

A sintered molding according to the invention is produced from the zirconia material according to the invention by means of essentially known conventional ceramic technology. The main process steps are, for example:
a) preparing a powder mixture according to the predetermined composition in water; optionally using liquefiers to prevent sedimentation;
b) homogenizing in a dissolver (high-speed stirrer);
c) milling in a stirrer ball mill thereby increasing the specific surface area of the powder mixture (=pulverizing and homogenizing);
d) possibly adding organic binders;
e) spray drying, resulting in pourable granules with defined properties;
f) moistening the granules with water and optionally additional press aids;
g) axial pressing, isostatic pressing of blocks or shaping that approximates the final contour using ceramic injection molding technology;
h) machining blocks in the green state or presintered state wherein the final contour is imaged extensively while taking into account the sintering shrinkage;
i) sintering (this may also take place in a 3-step sintering: 1. prefiring to a theoretical density of approximately 97%; the remaining pores are closed to the outside; 2. hot isostatic pressing at a high temperature and a high gas pressure, thereby practically complete final compaction; 3. so-called white firing, so that the disequilibrium created in the oxygen ions in the ceramic in hot isostatic pressing is compensated);
j) hard processing by grinding and polishing using diamond-tipped tools.

The zirconia material according to the invention can be used to produce sintered moldings, to produce artificial dental prostheses, dental restorations such as bridges, crowns, inlays and onlays, to produce dental root pins, implants, abutments, cages and spacers in the spinal cord field as well as unicondylar and bicondylar knee components. Use in the field of artificial dental prostheses and dental restorations is preferred. Use in the molar dental field is particularly preferred.

The amount of chemical stabilizers in the zirconia material according to the invention (amounts given relative to zirconia content) is 10 to 15 mol %, preferably 11 to 13 mol % for $CeO_2$; 1 to 5 mol %, preferably 2.5 to 3.5 mol % for $Sm_2O_3$ and $Gd_2O_3$. The total amount of chemical stabilizers in the zirconia material according to the invention comprising one or more additives, i.e., chemical stabilizers, wherein $CeO_2$ is preferred, $Sm_2O_3$ and $Gd_2O_3$ are particularly preferred. The total amount of chemical stabilizers is <15 mol %, preferably <14 mol %.

In the use of $CeO_2$ as a chemical stabilizer, the zirconia has an average structural grain size of 0.5 to 1.5 µm, preferably an average of 0.5 to 1.0 µm. It has surprisingly been found that the structural grain size can be reduced substantially by using $Gd_2O_3$ and $Sm_2O_3$. The structural grain sizes are preferably between 0.1 and 0.3 µm, especially preferably between 0.1 and 0.2 µm. Therefore a sintered molding according to a preferred embodiment contains zirconia crystals with an average size between 0.1 and 1.5 µm, preferably between 0.1 and 0.4 µm and especially preferably between 0.1 and 0.3 µm.

According to another embodiment of the invention, the zirconia may additionally contain soluble components. Soluble components may include, for example, Cr, Fe, Mg, Ca, Ti, Y, Ce, lanthanides and/or V. These components may function as color additives, on the one hand, and as sintering aids, on the other hand. The soluble components may be incorporated into the crystal lattice, i.e., substituted or deposited in the form of compounds, for example, in mixed crystals in the grain boundary phase.

The breaking strength of a sintered molding made of the zirconia material according to the invention is preferably ≥500 MPa, especially preferably ≥800 MPa.

It has surprisingly been found that the type and amount of the chemical stabilizer have a definite influence on the hardness of the zirconia material and also influence the fracture toughness.

The advantages of the novel material according to the invention in comparison with the prior art determined quantitatively on the basis of the improved "damage tolerance." Damage tolerance is a mechanical characteristic which describes the resistance of a material to an externally applied damage. The damage may take place in practice, for example, by grinding processing with diamond-tipped tools.

To measure the damage tolerance in the laboratory, damage is induced in the test body by means of a diamond tip (Vickers) under a defined strain force. Cracks develop in the region of the hardness indentation, so that the test body is weakened in this location. The weakening is determined quantitatively by measuring the residual breaking stress and/or residual strength at this location. The greater the residual strength after a defined weakening, the higher is the damage tolerance of the material.

For a detailed description of the damage tolerance, damage is induced in a series of test bodies using different stressing forces. This results in a characteristic line for the material (residual strength versus stressing force). An improved damage tolerance of a material in comparison with the prior art is detected by comparing these characteristic lines (see FIGS. 5 and 6).

It has surprisingly been found that the damage tolerance of the zirconia material is influenced by the type of chemical stabilizer. In the embodiments of the invention 94 to 99.9 vol % of the zirconia, preferably 98 to 99.9 vol %, is present in the tetragonal phase.

These findings are explained in greater detail below on the basis of figures and experimental series without restricting them:

The figures show:

FIG. 1: Diagram showing the hardness of sintered moldings made of zirconia as a function of the chemical stabilizer used.

Figure 2:
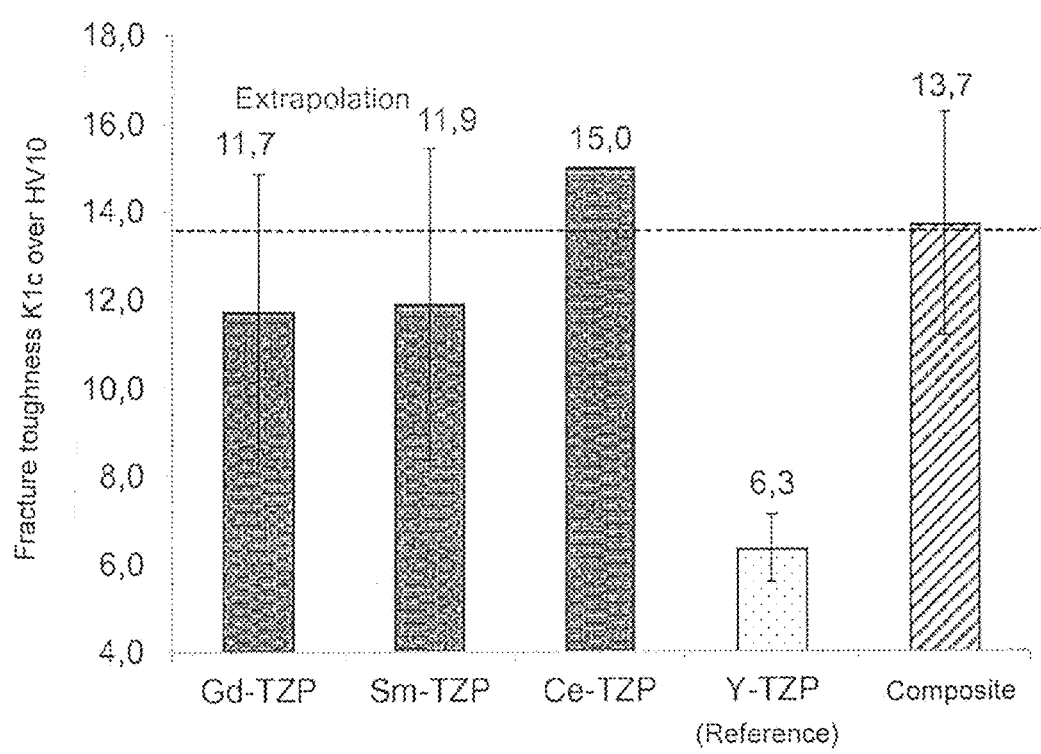

FIG. 2: Diagram showing the fracture toughness of sintered moldings made of zirconia as a function of the chemical stabilizer used.

Figure 3:
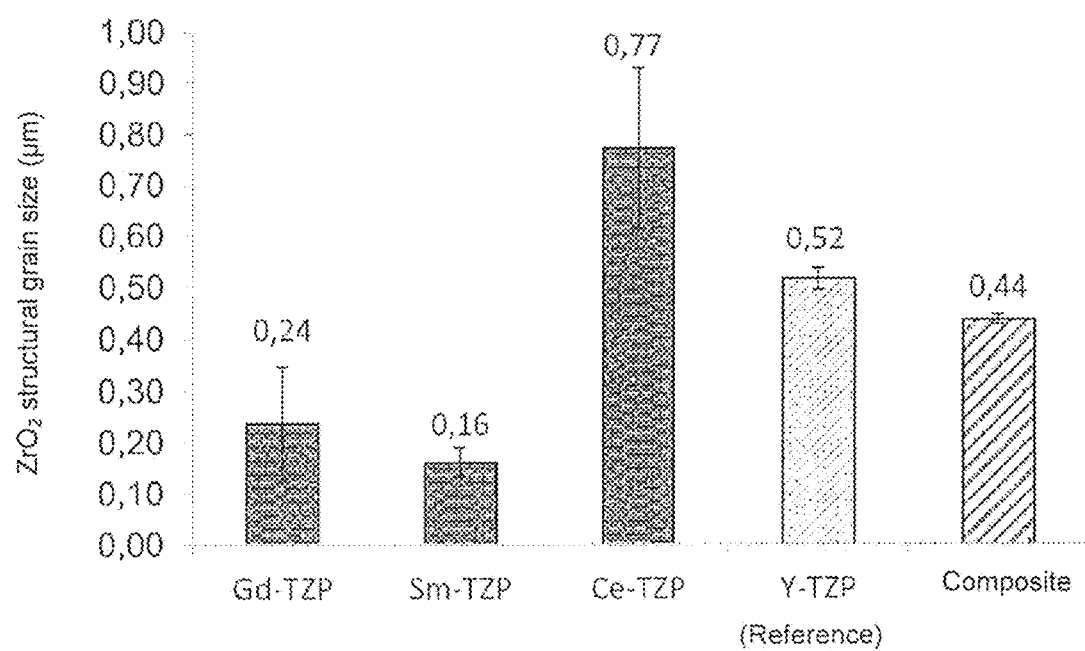

FIG. 3: Structural grain size as a function of the chemical stabilizer used.

Figure 4:
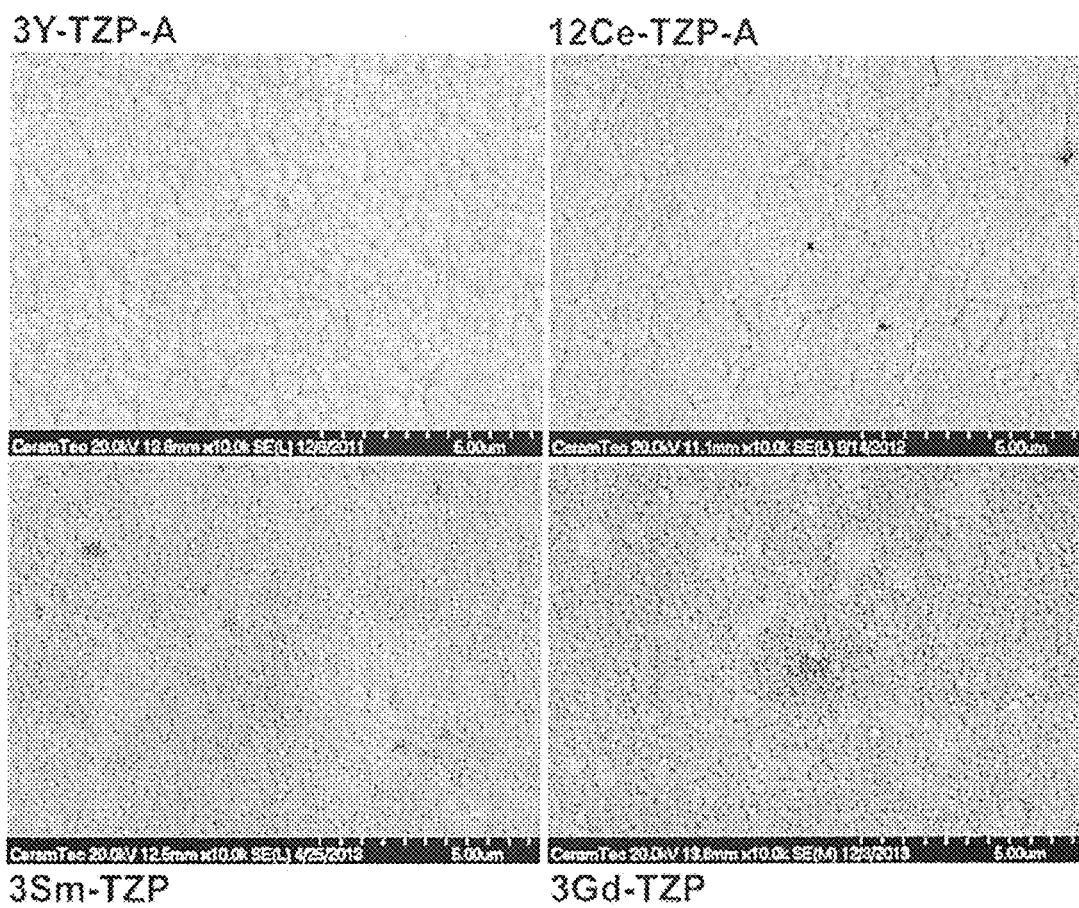

FIG. 4: Structure-forming agent as a function of the chemical stabilizer used.

Figure 5:
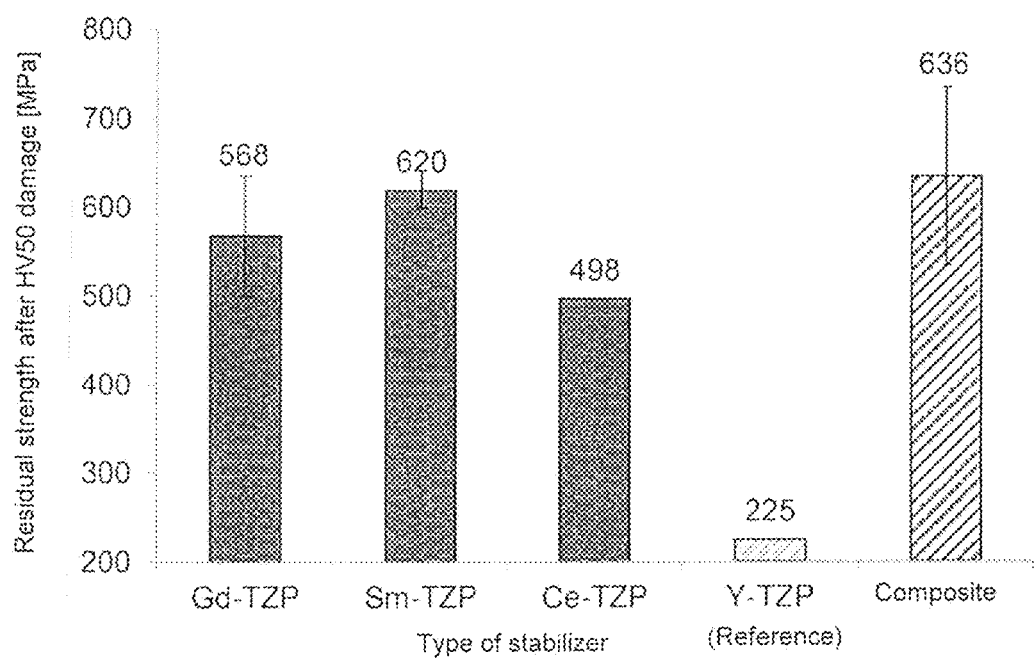

FIG. 5: Residual strength values after HV50 damage as a function of the chemical stabilizer used.

Figure 6:
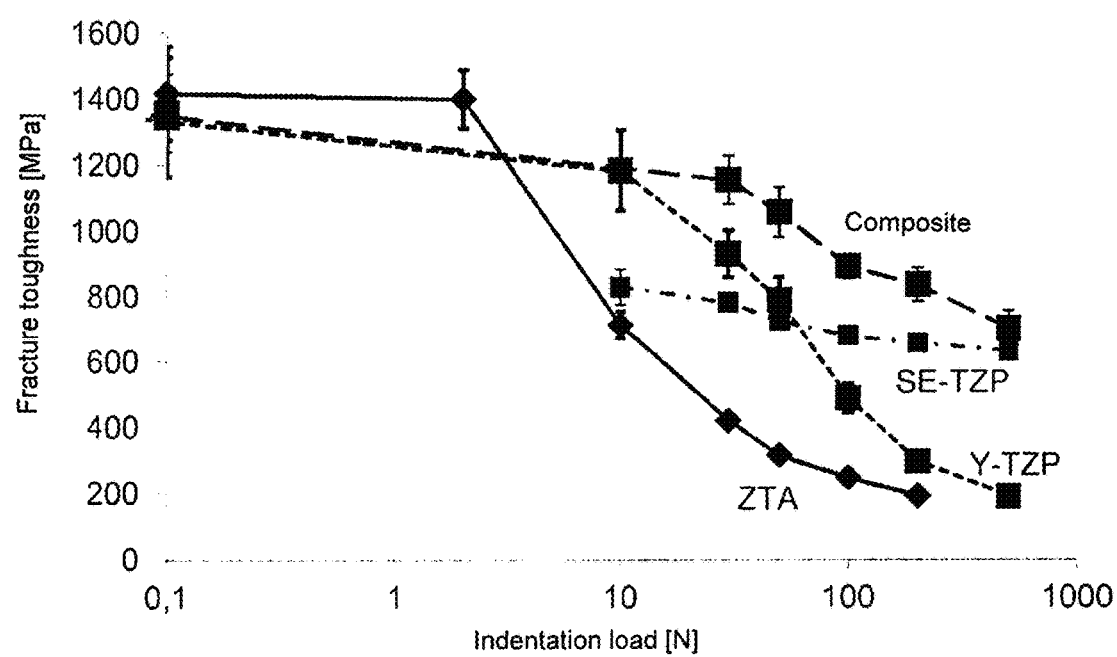

FIG. 6: Damage tolerance characteristic lines of zirconia materials according to the invention, composite material according to the invention and reference Y-TZP.

Figure 7:
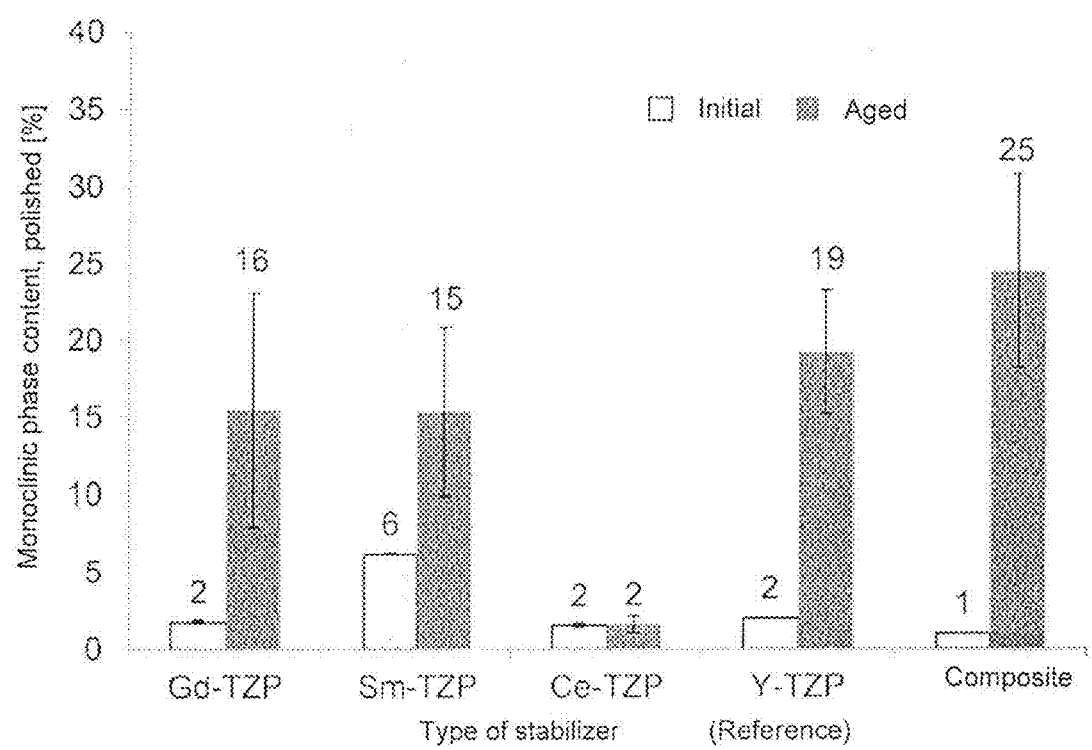

FIG. 7: Hydrothermal aging resistance as a function of the chemical stabilizer used.

EXPERIMENTAL SERIES 1

Hardness as a Function of the Chemical Stabilizer (FIG. 1)

FIG. 1 shows the results of an experimental series with chemical stabilizers according to the invention. The chemical stabilizers yttria ($Y_2O_3$), cerium oxide ($CeO_2$), samarium oxide ($Sm_2O_3$) and gadolinium oxide ($Gd_2O_3$) were tested along with a composite material according to the invention of strontium hexa-aluminate-reinforced zirconia (strontium hexa-aluminate-toughened zirconia). It has surprisingly been found that the variant with Ce stabilization has much lower hardness values in comparison with the Y stabilization. Samarium oxide and gadolinium oxide produce only a minor reduction in hardness, but this reduction is significant in the case of samarium oxide. The hardness was determined by means of a Vickers hardness test (HV10) with a force of 98.07 N.

With regard to the use according to the invention in the dental field, lower hardness values are desired. In the molar dental field, an artificial dental prosthesis made of Y-TZP, which is frequently used, may come in hard contact with a natural tooth. The hardness of Y-TZP is approximately 1250 (HV10). The natural tooth and/or the enamel has a definitely lower hardness of approximately 400 (HV10) because of the incorporated hydroxylapatite crystals. This difference in hardness can result in substantial abrasion of the natural tooth in a case of stress-related tooth grinding movement (bruxism). In addition, a lower hardness of the zirconia material facilitates damage-free hard processing. Therefore, another preferred embodiment of the invention comprises a zirconia material containing stabilizers which reduce the hardness of the zirconia material wherein the hardness of a sintered body produced from the zirconia material is less than 1250 (HV10), preferably less than 900 (HV10).

EXPERIMENTAL SERIES 2

Fracture Toughness as a Function of the Chemical Stabilizer (FIG. 2)

FIG. 2 shows an experimental series which represents the influence of the chemical stabilizer on the fracture toughness of the zirconia material. It has surprisingly been found that the use of cerium oxide ($CeO_2$), samarium oxide ($Sm_2O_3$) and gadolinium oxide ($Gd_2O_3$) as chemical stabilizers definitely increases the fracture toughness. The fracture toughness of the variants according to the invention was determined on the Vickers hardness indentation (HV10). The variants according to the invention with $CeO_2$ stabilization did not have any cracks at the hardness indentation. The variants according to the invention with $Sm_2O_3$ and $Gd_2O_3$ stabilization had few or no cracks at the hardness indentation. The variants which did not have any cracks at the hardness indentation are extremely tough zirconia materials. Their fracture toughness was estimated by extrapolation to 15 MPa*m^0.5. The range of extrapolated values is shown in FIG. 2 above a dotted line and relates to values above 13.4 MPa*m^0.5. This value is the highest measured fracture toughness that was measured with this determination method.

EXPERIMENTAL SERIES 3

Structural Grain Size and Structure-forming Agents as a Function of the Chemical Stabilizer (FIGS. 3 and 4)

FIGS. 3 and 4 show the influence of the chemical stabilizer on the structural grain size of the zirconia material according to the invention. The structure was evaluated using a scanning electron microscope. The grain size was determined according to the line cut method for determining the "mean cut length grain size" of a structural phase. It has surprisingly been found that, by using gadolinium oxide and samarium oxide, the structure of the material can be refined. Use of samarium oxide led to an average structural grain size of 0.16 μm. Use of gadolinium oxide led to an average structural grain size of 0.24 μm. The zirconia variant according to the invention with $Gd_2O_3$ stabilization shows local formation of coarse grains in the structural pattern (see FIG. 4). The individual coarse grains are present in the cubic zirconia phase, which slightly promotes the translucency of the material according to the invention in comparison with that of the dental standard Y-TZP.

EXPERIMENTAL SERIES 4

Damage Tolerance as a Function of Chemical Stabilizers (FIG. 5)

FIG. 5 shows zirconia materials according to the invention with different stabilizers. The x axis shows the various materials on the basis of the stabilizers used. The residual strength of the materials according to the invention after HV50 damage has been plotted in MPa on the Y axis.

It is clearly apparent that in the case of the zirconia materials according to the invention and composite materials, the residual strength values increase by a multiple in comparison with the reference material and/or the Y-TZP dental standard.

EXPERIMENTAL SERIES 5

Damage Tolerance Characteristic Lines of the Zirconia Material According to the Invention and Composite Material in Comparison with State-of-the-art Materials (FIG. 6)

FIG. 6 shows the residual strength values after different damages (here: Vickers hardness indentations with different loads of 3 to 500 N) of different material systems, a ZTA (zirconia-toughened alumina), a Y-TZP (Y-stabilized polycrystalline zirconia), a zirconia material Sm-TZP according to the invention and a composite material according to the invention (strontium hexa-aluminate-toughened zirconia). The tested indentation load has been plotted logarithmically in Newtons on the x axis as a function of the residual moisture in MPa on the y axis.

In comparison with materials from the prior art, it is found that the novel materials according to the invention have significantly higher damage tolerance after different damage loads with a uniform initial strength.

EXPERIMENTAL SERIES 6

Hydrothermal Aging Resistance as a Function of the Chemical Stabilizer (FIG. 7)

FIG. 7 shows the hydrothermal aging resistance of the zirconia materials according to the invention as a function of the stabilizer used. To do so, the monoclinic phase component before and after aging was measured on polished sintered moldings by means of X-ray diffractometry.

The moldings were stored in hydrothermal atmosphere in an autoclave at 134° C. and 2.2 bar pressure, running through a cycle of 10 hours.

It has surprisingly been found that the variant according to the invention with $CeO_2$ stabilization does not exhibit any hydrothermal aging. The variants according to the invention with $Sm_2O_3$ and $Gd_2O_3$ stabilization show a slight but significant improvement in the hydrothermal stability in comparison with the reference material Y-TZP.

Thus the zirconia material according to a particularly preferred embodiment of the invention has an improved hydrothermal aging resistance. The improved aging resistance is manifested in the fact that the amount of monoclinic zirconia in the total zirconia content amounts to less than 17 vol % and preferably less than 10 vol % and especially preferably less than 5 vol % after storage in a hydrothermal atmosphere in an autoclave at 134° C. and 2.2 bar pressure with a cycle of 10 hours.

The advantages of the zirconia material according to the invention are summarized again in the following section:

- the zirconia material according to the invention and sintered moldings according to the invention are produced by means of the known conventional ceramic technology
- 3-step sintering (prefiring, HIP, white firing) is possible, resulting in a greater strength
- no hydrothermal aging due to the use of $CeO_2$ as a chemical stabilization
- damage-free hard processing, in particular mechanical hard processing of densely sintered or partially sintered intermediate products is possible
- easier hard processing due to lower material hardness (equivalent to less tool wear)
- lower hardness therefore definitely reduced abrasion of the natural antagonist in the molar area, among other things
- use as a fully anatomical system is possible, i.e., veneers are not needed in the molar area, therefore additional cost savings for the patient and reduction in the risk of chipping of parts of the veneer (chip off)
- aesthetics suitable for dental standards
- compensation for lack of resilience (damping and/or elasticity of the tooth in chewing action) in the case of a complete dental restoration with implant, i.e., definitely reduced buildup of stress with a chewing action
- zirconia material can be used to produce blanks and/or blocks for CAD/CAM processing in the presintered or densely sintered condition use of the sintered moldings as dental prostheses, for example, restorations (bridges, crowns, inlays, onlays), as dental root pins, implants, abutments
use to produce spinal cages, medical instruments, etc.

The invention claimed is:

1. A zirconia material comprising:
   zirconia; and
   a chemical stabilizer;
   wherein 70 to 100 vol % of the zirconia is present in a tetragonal phase, and wherein the chemical stabilizer comprises at least one oxide of a rare earth metal and wherein the chemical stabilizer chemically stabilizes the tetragonal phase;
   wherein the content of zirconia is between 94 and 96 vol %; and
   wherein the zirconia material comprises a second main component is present with a volume amount between 4 and 6 vol %, wherein the second main component consists of a relative amount of more than 80 vol % strontium aluminate or lanthanum aluminate, and
   wherein the chemical stabilizer is selected from the group consisting of $Sm_2O_3$ and $Gd_2O_3$.

2. The zirconia material according to claim 1, wherein the chemical stabilizer is $Sm_2O_3$.

3. The zirconia material according to claim 1, wherein 94 to 99.9% of the zirconia is present in the tetragonal phase.

4. The zirconia material according to claim 1, wherein 98 to 99.9% of the zirconia is present in the tetragonal phase.

5. The zirconia material according to claim 2, wherein the $Sm_2O_3$ is present in an amount between 1 and 5 mol % relative to the zirconia content.

6. The zirconia material according to claim 1, wherein the chemical stabilizer is $Gd_2O_3$ and is present in an amount between 1 and 5 mol % relative to the zirconia content.

7. The zirconia material according claim 1, wherein the chemical stabilizer content is <15 mol %.

8. The zirconia material according to claim 1, wherein the zirconia comprises a soluble constituent.

9. The zirconia material according to claim 1, wherein the zirconia comprises a soluble constituent comprising a member selected from the group consisting of a Cr compound, a Fe compound, a Mg compound, a Ca compound, a Ti compound, an Y compound, a Sc compound, a lanthanoid compound and a V compound.

10. The zirconia material according to claim 1, wherein the second main component consists of strontium aluminate.

11. The zirconia material according to claim 1, wherein the zirconia material has a hardness of less than 1250 (HV10).

12. The zirconia material according to claim 1, wherein the zirconia material has a breaking strength of ≥500 MPa.

13. The zirconia material according to claim 1, wherein the zirconia material has a breaking strength of ≥800 MPa.

14. The zirconia material according to claim 1, wherein the damage tolerance and/or residual strength after HV50 indentation is >400 MPa.

15. The zirconia material according to claim 1, wherein the zirconia material has an improved hydrothermal aging resistance, wherein the amount of monoclinic zirconia in the total zirconia content amounts to less than 17 vol % after storage in a hydrothermal atmosphere in an autoclave at 134° C. and 2.2 bar pressure and a cycle of 10 hours.

16. A sintered molding comprising the zirconia material according to claim 1 that has been molded and then sintered to form a sintered molded product, wherein the sintered molding is densely sintered or partially sintered, and wherein the sintered molded product can be mechanically processed without being damaged.

17. An artificial dental prosthesis, spinal implant or medical instrument comprising the sintered molding of claim 16.

18. A dental restoration comprising the zirconia material of claim 1, wherein the dental restoration is selected from the group consisting of a bridge, a crown, an inlay, an onlay, a tooth root pin, an implants and an abutment.

19. The zirconia material according to claim 1, wherein the chemical stabilizer is $Gd_2O_3$.

* * * * *